(12) United States Patent
Babic

(10) Patent No.: US 8,902,425 B2
(45) Date of Patent: Dec. 2, 2014

(54) TEMPERATURE-STABLE INCOHERENT LIGHT SOURCE

(71) Applicant: Dubravko Ivan Babic, Santa Clara, CA (US)

(72) Inventor: Dubravko Ivan Babic, Santa Clara, CA (US)

(73) Assignee: University of Zagreb, Zagreb (HR)

( * ) Notice: Subject to any disclaimer, the term of this patent is extended or adjusted under 35 U.S.C. 154(b) by 0 days.

(21) Appl. No.: 13/857,273

(22) Filed: Apr. 5, 2013

(65) Prior Publication Data

US 2013/0265584 A1   Oct. 10, 2013

Related U.S. Application Data

(60) Provisional application No. 61/621,567, filed on Apr. 8, 2012.

(51) Int. Cl.
*G01B 9/02* (2006.01)
*G01N 21/53* (2006.01)

(52) U.S. Cl.
CPC .......... *G01B 9/02055* (2013.01); *G01N 21/532* (2013.01); *G01N 2201/0683* (2013.01); *G01N 2201/1211* (2013.01)
USPC ............ 356/364; 356/369; 356/368; 356/491

(58) Field of Classification Search
CPC ............. G01B 9/02055; G01N 21/532; G01N 2201/0683; G01N 2201/1211
USPC .......... 356/364–369, 491, 487; 250/205, 239; 372/20, 32, 33; 359/237, 642
See application file for complete search history.

(56) References Cited

U.S. PATENT DOCUMENTS

| | | | | |
|---|---|---|---|---|
| 4,733,094 A | * | 3/1988 | Carpentier et al. | 250/551 |
| 5,367,399 A | * | 11/1994 | Kramer | 359/206.1 |
| 5,754,571 A | * | 5/1998 | Endoh et al. | 372/20 |
| 6,534,756 B1 | * | 3/2003 | Grimbergen | 250/205 |
| 6,807,205 B1 | * | 10/2004 | Albrecht et al. | 372/33 |
| 2003/0066946 A1 | * | 4/2003 | Grimbergen | 250/205 |
| 2007/0063125 A1 | * | 3/2007 | Downing | 250/205 |
| 2012/0025714 A1 | | 2/2012 | Downing | |

* cited by examiner

*Primary Examiner* — Sang Nguyen
(74) *Attorney, Agent, or Firm* — Shalini Venkatesh

(57) ABSTRACT

Embodiments generally relate to a light source and methods for minimizing temperature sensitivity of a light source light source. In one embodiment a light source includes a light-emitting diode, a light beam having an optical axis, a photodetector and a polarizer. The diode is operatively configured to emit the light beam. The beam splitter, positioned to intercept the light beam, includes a first optical surface operatively configured to reflect a first portion of the light beam and to transmit a second portion of the light beam therethrough. The photodetector is positioned to capture the first portion of the light beam after reflection by the beam splitter and operatively configured to generate photocurrent proportional to an intensity of that captured first portion. The polarizer is positioned between the diode and the beam splitter, and is operatively configured to polarize the light beam along a polarization direction perpendicular to its optical axis.

7 Claims, 6 Drawing Sheets

TEMPERATURE-STABLE INCOHERENT LIGHT SOURCE

CROSS REFERENCE TO RELATED APPLICATION

This application claims priority to U.S. Provisional Patent Application Ser. No. 61/621,567, entitled "Temperature-stable incoherent light source", filed on Apr. 8, 2012, which is hereby incorporated by reference as if set forth in full in this application for all purposes.

BACKGROUND OF THE INVENTION

Constant-intensity-light sources are ubiquitous in optical sensing systems used in medical, environmental, and industrial applications. Temperature stability of these optical sources is essential as it is the foundation of the instrument accuracy, be it through calibration at manufacturing time or in real time correction. Optical and electrical properties of all light emitting components and optical materials vary with temperature. For this reason an absolutely stable source does not exist. Rather, sources of varying stability are developed for specific applications. In many applications today, and specifically, in turbidimeters and nephelometers, light-emitting diodes are used to provide constant light output with reliability, accuracy, and power efficiency that surpasses incandescent lamps used in the same instruments historically. This invention disclosed in this application is an improved design of a constant-intensity light source that uses an LED. The invention may be used for many applications, but it will be described as implemented in turbidity and/or nephelometry.

Turbidity is an expression of the optical properties of a liquid that causes light rays to be scattered and absorbed rather than transmitted in a straight line through a sample. In other words, turbidity is a measure of muddiness or cloudiness of water. One also speaks of turbidity measurement when characterizing the physical attributes of a colloidal suspension. When a light beam is incident on a colloidal suspension of undissolved finely distributed particles, the suspended particles scatter the light in all directions. The scatter depends on the size of the particles and the spectral properties of the light used to make the measurement. Turbidimeter is a device that is used for quantifying the turbidity of liquids. This measurement is generally performed optically and the units are established based on optical transparency and scattering.

The intensity of scattered light is affected by many variables including wavelength, particle size, color, and shape. The water treatment authority considers all particles of less than 0.45 microns in diameter as being dissolved, but particles smaller than 0.45 microns will also scatter light. The amount of scattered light is not the same in all directions and the spatial distribution pattern varies with particle size. Scattering distribution patterns show that when particles are equal to or larger than the wavelength of the incident light beam, there is a higher amount of forward scattered light, but as the particle size becomes smaller the scattering in all directions prevails so that particles smaller than 0.05 microns in diameter (colloids) scatter light equally in all directions. Other factors that influence light scattering are particle color, particle shape, difference between the refractive indexes of the particle and the sample fluid.

Turbidity measurements are performed on a vial containing the liquid under test or across a transparent pipe through which the liquid under test flows. FIG. 1(a) shows schematically the block diagram of optical measurements that may be performed during a turbidity test. The liquid under test is located or flows inside the pipe (or vial) 101 with transparent walls. A collimated light beam 102 is emitted from a light source 103, directed through the pipe 101 and is detected at a transmitted-light detector 104. Comparing the intensity of the light 103 emitted from the source and the intensity of the light detected by the transmitted light detector 104 gives information about the absorptance of the liquid in the pipe 101. The absorption may be a result of light scattering out of the collimated beam in which case this light can be detected at a right angle away from the original beam direction, in the 90-degree detector, also referred to as the nephelometric detector. When light-scattering in the sample is weak, the reduction of the intensity detected by the transmitted-light detector 104 is small relative to the starting beam intensity 102 and often becomes comparable to the stability drift of the optical source. The stability of the optical source hence directly limits the ability of the turbidimeter to quantify very low turbidity values. In this situation, the 90-degree detector may provide more accurate reading as the in low turbidity samples a small amount of light that scatters sideways has the same stability drift as the original source. However, signal to noise ratio for the nephelometeric detector is worse because the low level light here detected may become comparable to the stray light scattered around the measurement unit and the optics. Further measurement positions, shown in FIG. 1A, can be used to improve the accuracy: Forward scattering 106 and backward scattering 107 of light from the sample holder.

A turbidity measurement basic instrument design uses a single light source and a single photodetector located at 90 degrees to the transmitted light as shown in FIG. 1a with light path 103-101-105. Although very simple, this design has the inherent problem in that the stability of the light source 103 (due to ageing and temperature changes) directly degrades the accuracy of the reading. Repeated calibrations are needed to maintain accuracy. Using ratios of multiple detectors and multiple sources increases the accuracy and stability of measured turbidity values. Some of the practical methods are the Dual-Beam Method (DBM) and Modulated Four-Beam Method (MFBM). The DBM uses a single light source which is split by an oscillating minor into a measuring beam and a reference beam. The measurement is made differentially with a single photodetector detecting the different light intensities of both beams. This method reduces the need for frequent calibration and, when used with a monochromatic light source, totally eliminates the need for calibration. The accuracy is maintained if all the optical components in the system (including the mirror that switches the beam direction) are stable with temperature and ageing (reflections/refractions in the light path). Still the only value measured is the ratio of the transmitted to scattered light intensity. The MFBM uses two light sources and two photodetectors spaced at 90° intervals around a circular sample chamber. Sequentially, the sensor accomplishes two measurements. The two light sources light up alternatively, and when each of them is lit, two of the detectors (one straight forward and one at 90-degrees as detectors 104 and 105 in FIG. 1a, respectively) measure light intensity. These four measurements are sufficient to evaluate the ratio between the transmitted to scattered light intensities without the need for calibration and independent of individual conversion efficiencies of the detectors and the light-sources. Even with four measurements, the only quantity obtained is the ratio of transmitted to scattered light.

Although turbidity measurement technology is well developed and commercialized there still are specific applications for which improvements are needed. First, the complete evaluation of optical scattering properties of the fluid requires determining the transmitted and the scattered light independently. Secondly, reducing power consumption by using only one light source and no microprocessor to handle data analysis enables battery powering which is essential for portable use. Both of these improvements are needed without loss of accuracy and with no repeated calibration.

This application discloses a modification of standard optical sources used in turbidimeters (incandescent lamps and light-emitting diodes) which results in an improvement in the light-source stability against temperature drift and ageing. This improvement enables more accurate nephelometric measurements in all configurations presented.

A typical closed-loop control of the light-output from a light source such as incandescent lamp, light-emitting diode, or laser is illustrated in FIG. 1B. A light source 201 is powered by control electronic 206 and emits a collimated light beam 205 onto a beam splitter 202. The transmitted portion of the beam 203 is useful light to be used for measurement and sensing. The reflected portion 204 of the incident light is captured by the photodetector 207. The intensity of the reflected beam 204 is converted to electric current 205 in the photodetector 207. The control electronics 206 compares the reflected beam intensity in form of current 205 against a reference 208.

The primary factors producing intensity drift in the output beam intensity versus temperature are (a) temperature drift in the reference 208, (b) the change in the emission wavelength or emission spectra of the light source so that the transmittance to reflectivity ratio of the beam-splitter changes with temperature, and (c) scattered light reaching the detector and offsetting the measured power is also temperature dependent.

An important factor coming to play when the optical source is a single-mode laser that emits monochromatic and coherent output beam: Interference fringes appearing on transparent objects external to the source. If the optical source 103 in FIG. 1a is a single-mode laser with a coherent beam, the passage of the light through the walls of the vias or the pipe 101 containing a liquid will produce interference fringes—modulation in transmission that changes with wavelength and hence indirectly with temperature. The interference fringes produce loss of correlation between the different reflections/transmission measurements of the light beam 102 and degrade measurement sensitivity. If interference is a problem in the measurement setup, as it is in turbidity measurement, there is an advantage in using incoherent optical sources. Light-emitting diodes have coherence length which is significantly smaller than the thickness of the walls on most glass pipes and test vials. For this reason, interference fringes rarely occur in the measurement.

BRIEF DESCRIPTION OF THE INVENTION

We now briefly describe the improvement in the stability of an LED or incandescent optical light source with a feedback control-loop. Suppose one built an optical source based on FIG. 1B and used uncoated beam splitter. We refer to this system as the baseline system (PRIOR ART). One measures the output power versus temperature over a temperature range. The drift or variation in the output intensity results from, among many effects, the temperature drift and wavelength drift in the detector responsivity, the reference source, the control electronics, and finally some temperature dependence of the refractive index in the glass in the beam splitter. The wavelength drift occurs because the peak emission wavelength of the light-emitting diodes drifts with temperature and hence the temperature effects are two fold: temperature performance of the components changes, but also the optical constants of the devices and materials change with wavelength. The wavelength drift is a direct function of the light-emitting diode temperature: these two are deterministically related, but experimentally determined. The peak emission wavelength of LEDs is very temperature sensitive $d\lambda/dT \approx$ several nanometers per ° C. Using this knowledge, one can use the wavelength dependence of the transmission/reflectivity ratio of the coating on the splitter to compensate for the temperature drift of all other components. Therefore measuring the baseline temperature and wavelength drift using an uncoated beam splitter, one can design a beam splitter coating so that it matches the drift in opposite direction. In this way, the temperature drift of the source is countered by the changes of the optical properties of the beam splitter. We refer to this as the first level compensation; it is based on making an optical coating (on the beam splitter) whose transmission/reflection ratio to unpolarized light approximately matches the temperature dependence of the baseline system. If we denote with P the output intensity of the light source 203 (or 303, 414, 514 in later figures), then output-intensity local temperature sensitivity is $dP(T)/dT$, defined at every temperature, and output-intensity temperature sensitivity is defined with $(P(T_2) P(T_1))/(T_2 T_1)$, where $T_1$ and $T_2$ are the temperatures at the boundary of the defined temperature range and $P(T_1)$ and $P(T_2)$ are the intensities of the output beam at temperatures $T_1$ and $T_2$, respectively.

In one embodiment of the present invention, the second level of compensation is realized by using a polarizer between the light-emitting diode and the beam splitter and employing an interference coating on the beam splitter such that for at least a first polarization direction of the polarizer, the output-intensity temperature sensitivity is always positive, while for a second polarization direction that is perpendicular to the first polarization direction, the output-intensity temperature sensitivity is always negative. In this way, there is always a polarization between the first and the second for which the output-intensity temperature sensitivity is at minimum.

DETAILED DESCRIPTION OF THE INVENTION

Figure 1A:
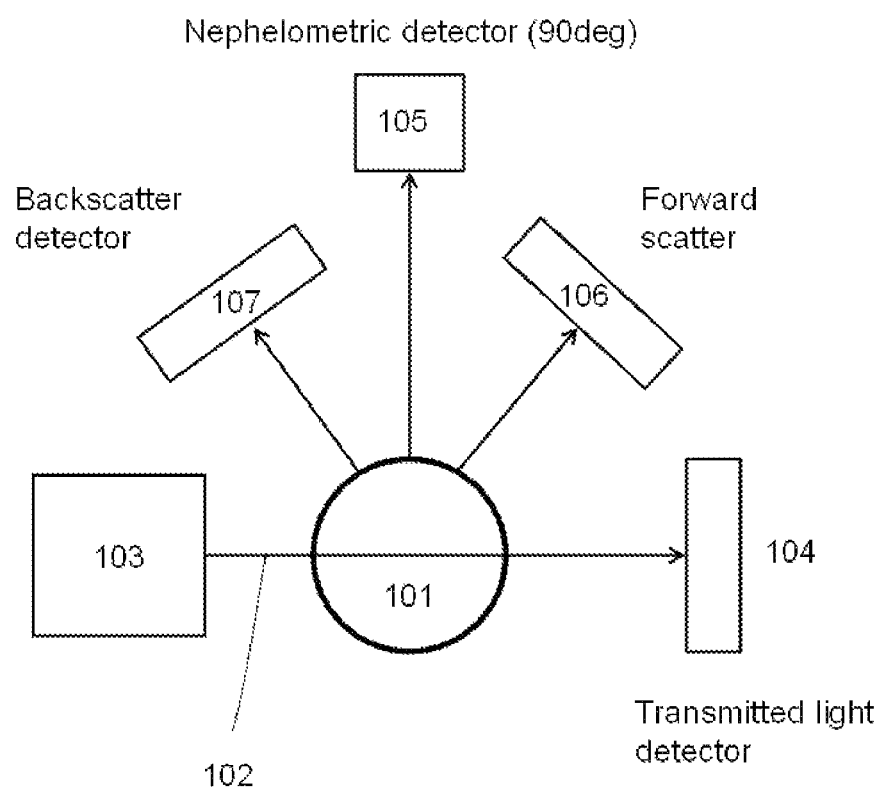
FIG. 1: (a) Types of measurements used in turbidimetry (PRIOR ART), and (b) Simplified schematic showing a classic optical source stabilized using a feedback control loop (PRIOR ART).
Figure 1B:
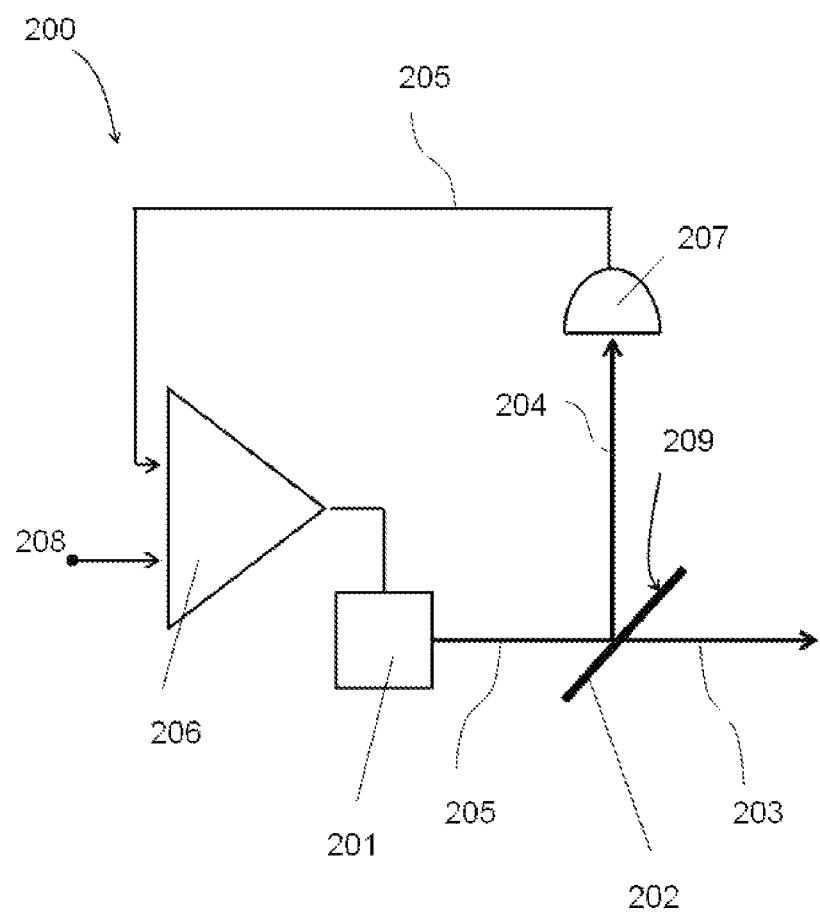
Figure 2:
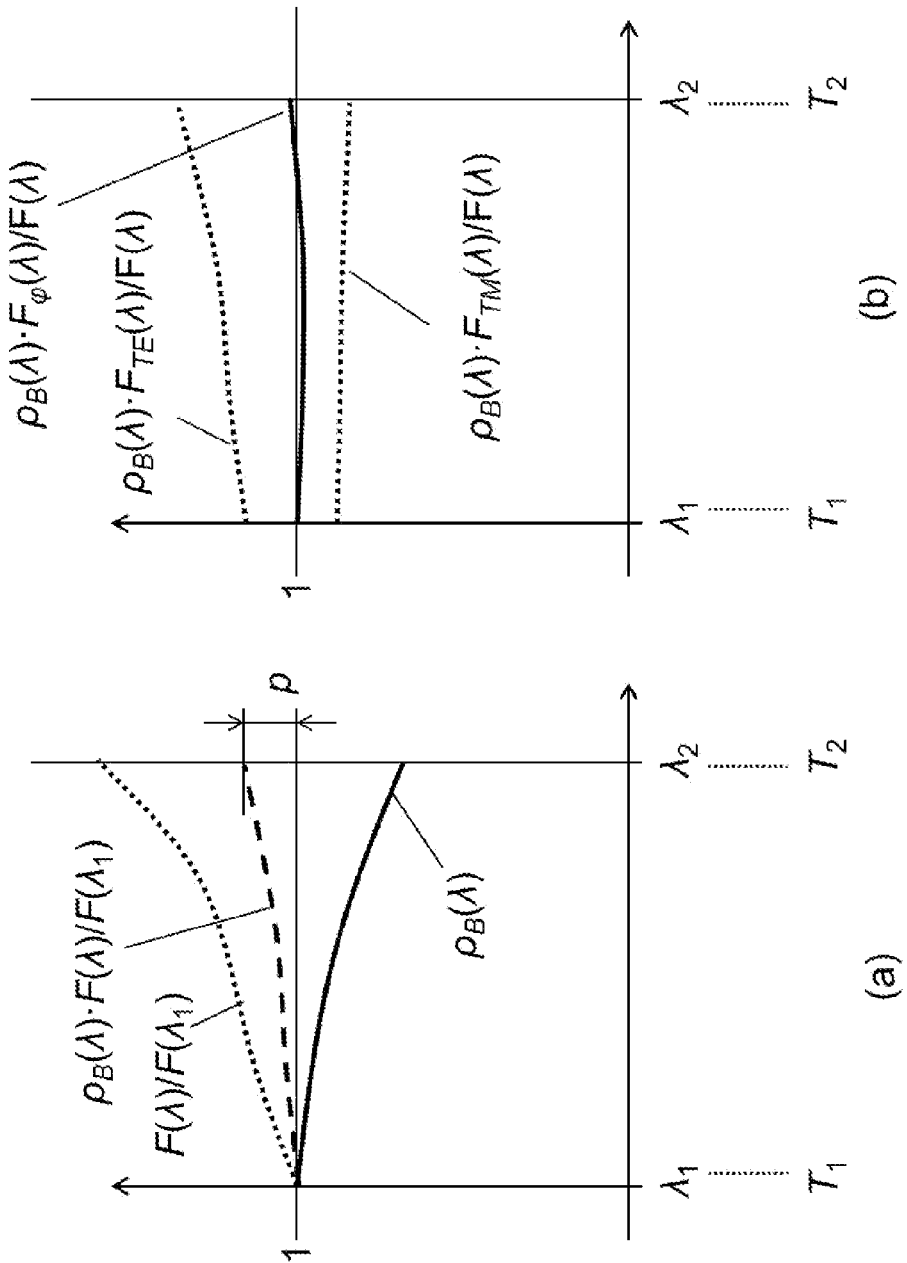
FIG. 2: Graphs explaining the optimization of the beam-splitter interference coating.

The improvement in the stability of an LED or incandescent optical light source with a feedback control-loop is based on several elements. We explain this in more detail in this section. Suppose one built a control loop system as shown in FIG. 1B and characterized it over a temperature range between $T_1$ and $T_2$ ($T_2 > T_1$). Between these two temperatures, the peak emission wavelength varies between $\lambda_1$ and $\lambda_2$ ($\lambda_2 > \lambda_1$). The beam splitter is an uncoated glass slide or a prism. The light hitting the beam splitter is unpolarized, hence the only variation in output intensity with temperature will come from the wavelength dependence of the optical characteristics and temperature dependence of the electronic components. This is referred to as a baseline test. During the baseline test, the output intensity is measured over the temperature range and is normalized to its value at the starting temperature or wavelength: $\rho_B(\lambda) \equiv P(\lambda)/P(\lambda_1$, where subscript B stands for "baseline". If many devices are used to acquire data for the baseline test, then there is a family of $\rho_B(\lambda)$ curves denoted $\rho_B(\lambda)$ and one has to consider the envelope of all curves rather than just a single curve. Here the temperature is encoded in wavelength variation. FIG. 2a illustrates $\rho_B(\lambda)$ as a function of wavelength and temperature.

In one embodiment, the data from the baseline test is used to design a coating for the beam-splitter. A tolerance margin $0<p<1$ is selected. The tolerance margin is set low ($p<0.01$) when one desires a coating with tight tolerances and a good match to the already characterized (baseline test) temperature dependence of the optical source. It is set loose (eg. $p<0.2$) to relax the specifications on the coating required for the beam splitter, but will also result in lower stability once the light source is optimized.

Figure 3:
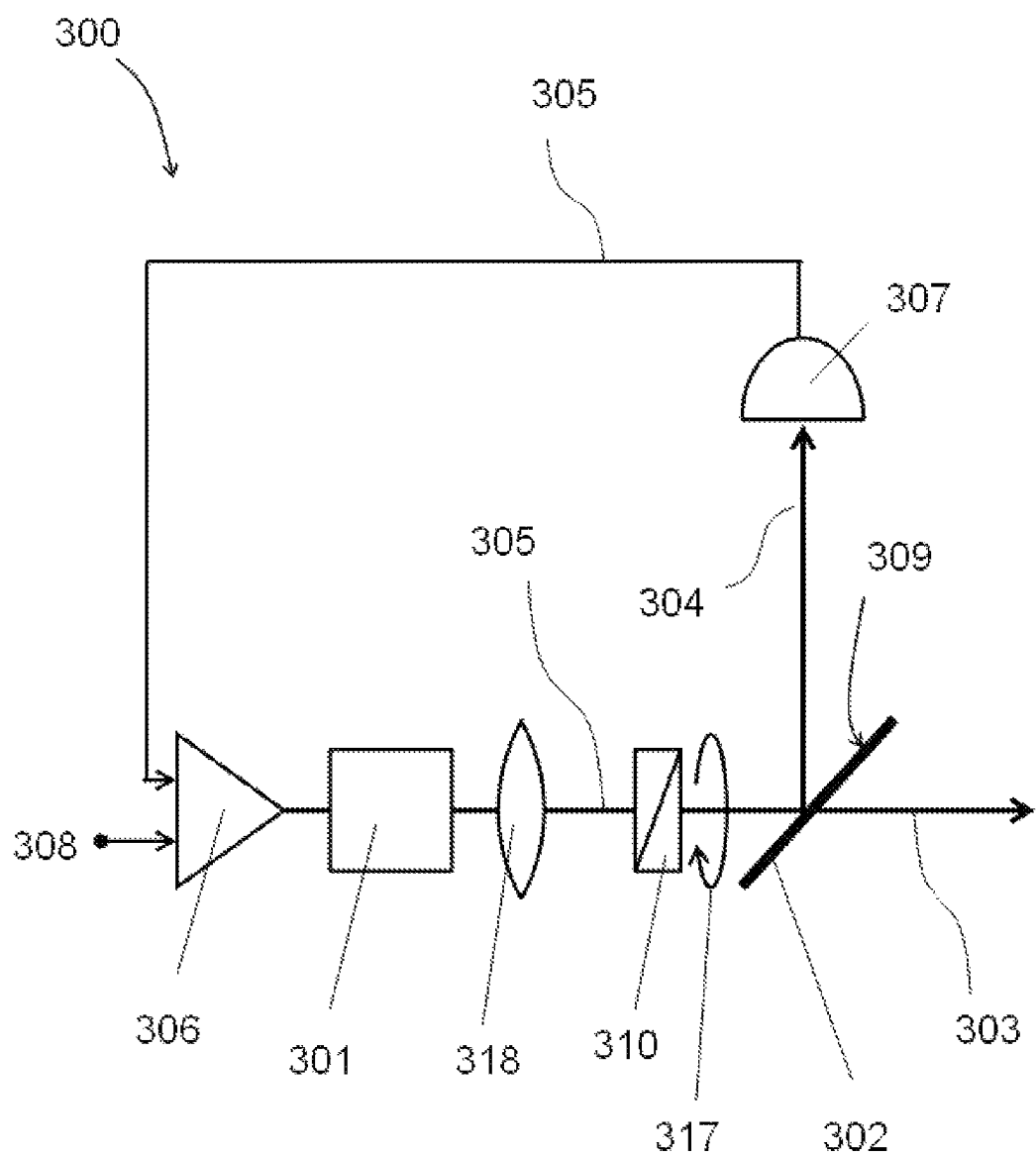
FIG. 3: One embodiment of the optical source using the present invention.

The output power from the source in the feedback configuration shown in FIGS. 1B and 3 is proportional to the ratio of the transmitted to reflected beam intensities at the beam splitter. We refer to this ratio as factor F and we use it to compensate the temperature effect on the output intensity coming from all other components. To specify the coating, we introduce and use two quantities: $F_{TE}(\lambda)$ and $F_{TM}(\lambda)$ as the ratios of the transmitted to reflected beam intensities for TE and TM polarized waves at the coating. Each of these quantities is a function of the wavelength. TE polarization means that the electric field is transverse (perpendicular) to the plane of incidence at the beam splitter. At every wavelength the intermediate values of F are given below, where $\phi$ is the polarization angle. Assuming the coating is lossless, we have $$F_\phi(\lambda) = \frac{2(1+F_{TE})(1+F_{TM})}{(1+F_{TE})+(1+F_{TM})-(F_{TM}-F_{TE})\cos 2\phi} - 1 \quad (1)$$

Here $F_{TE}$ and $F_{TM}$ are the extreme values of F at a given wavelength: $F_{TM}=F_0(\lambda)$ and $F_{TE}=F_{\pi/2}(\lambda)$. When light incident on the beam splitter is not polarized, we have to average (1) over all the polarization angles, as they are equally likely. This gives the factor F for unpolarized light $$F(\lambda) = \sqrt{(1+F_{TE})(1+F_{TM})} - 1 \quad (2)$$

The output intensity for the system shown in FIG. 1B with this new coating disposed on the beam splitter is proportional to the product $\rho_B(\lambda)F(\lambda)$. To match the temperature dependence of the baseline system, the coating has to be designed so that for a given $\rho$ we have $$\left|1 - \frac{F(\lambda)}{F(\lambda_1)}\rho_B(\lambda)\right| < p \quad (3)$$

These quantities are shown in FIG. 2b along with the product $\rho_B(\lambda)F(\lambda)/F(\lambda_1)$. The condition (3) will ensure that the coating matches the temperature dependence with unpolarized light.

The key innovation described in this application is improving the stability beyond what has been specified with equation (3). This is accomplished by polarizing the light beam coming from the light-emitting diode and using the polarization direction as another adjustment variable. Interference coatings generally contain multiple optically thin films and their reflectivity/transmission are polarization and wavelength dependent. For this reason, the output power from the light-source with the polarization direction set parallel to the plane of incidence of the surface of the beam splitter with the interference coating may be dramatically different from the case when the polarization direction is set perpendicular to the plane of incidence of the beam splitter. With proper adjustment of the coating properties it is possible to make the deviations for parallel and perpendicular polarizations sufficiently different and of opposing temperature drift coefficients so that adjusting the polarization through angles between the two extremes (TM and TE) allows reaching an optimal, minimum temperature drift coefficient. FIG. 2b illustrates an example where for TM and TE polarizations, the output power (proportional to $\rho_B(\lambda)F_{TM}(\lambda)/F(\lambda_1)$ or $\rho_B(\lambda)F_{TE}(\lambda)/F(\lambda_1)$) results in temperature drift coefficients of different polarity. By adjusting the polarization to an angle between TE and TM, one is able to minimize the temperature drift as shown in the optimal case $\rho_B(\lambda)F_\phi(\lambda)/F(\lambda_1)$ in FIG. 2b.

An exemplary view of light-source 300 utilizing the innovative concept is shown in FIG. 3 comprises an light-emitting diode 301 emitting light 305 through a collimating lens 318 and a polarizer 310 whose optical axis is substantially parallel to the light beam 305, a beam splitter 302 with an interference coating 309 on the surface facing the light emitting diode 301, a detector 307 which captures a portion 304 of the beam 305 that has been polarized by the polarizer 310 and reflected on the beam splitter 302. Another portion of the light beam 305 is polarized by the polarizer 310 and transmitted through the beam splitter 302 to the outside world as beam 303. The polarizer is operatively configured to be able to rotate around its optical axis which is or is near parallel to the light beam 305. Once a desired polarization direction is found, the polarizer can be fixed to keep the specified polarization direction indefinitely. In other words, the polarization direction can be adjusted and set at manufacturing time or possibly corrected if need at a later time. The interference coating 309 on the beam splitter 302 is specially designed to enable the adjustment in polarization direction of the polarizer 310 to alter the temperature drift coefficient of the optical light source 300. The light-emitting diode 301 may have a lens integrated with it. The lens may or may not be an integral part of the light-emitting diode, but it is understood that when a light-emitting diode is used a collimating lens 318 is used in front of it whether integrated or not.

There are many ways a coating may be designed to accomplish the temperature drift compensation. In one embodiment, an additional constraint on the coating is made: The difference between $F_{TE}(\lambda)$ and $F_{TM}(\lambda)$ should always be sufficient to cause an effect on the output intensity by changing the polarization of the LED using the polarizer. This means that for all wavelengths (and temperatures) we have, $$|F_{TM}(\lambda) - F_{TE}(\lambda)| > p \cdot F(\lambda) \quad (4)$$

In addition, the final design has to be such that the predicted output intensity slope changes sign when the polarization direction changes from TE to TM.

$$\frac{d}{d\lambda}\left(\frac{F_{TE}(\lambda)}{F(\lambda_1)}\rho_B(\lambda)\right) \times \frac{d}{d\lambda}\left(\frac{F_{TM}(\lambda)}{F(\lambda_1)}\rho_B(\lambda)\right) < 0 \quad (5)$$

When polarized beam is incident onto the beam splitter, and the F value can be varied by rotating the polarizer, i.e., changing the polarization of the incoming beam. Once the beam splitter has been designed and inserted as shown in FIG. 3, a measurement can be made of the temperature stability (evaluating $\rho_\phi(T)$ for different polarization directions). The relationship (5) will lead to the condition that can be checked on the completed light-source:

$$\frac{d\rho_{TE}(T)}{dt} \times \frac{d\rho_{TM}(T)}{dt} < 0 \qquad (6)$$

Here $\rho_{TM}(T)$ and $\rho_{TE}(T)$ are the normalized output intensities versus temperature when the polarizers are set to TM and TE polarization direction, respectively. Equation (6) says that the slopes in the normalized output intensity versus temperature curves, when the polarizer is set to TM and TE, have opposite sign. The polarizer is mechanically attached in a manner that allows it to rotate around its optical axis to let one change the polarization direction of the emitted light, while not changing the polarizer's optical axis.

The polarization direction is adjusted by finding the minimum temperature sensitivity of the output intensity. This means finding $\phi$ for which $|1-\rho_\phi(T)|$ is minimal when T varies between $T_1$ and $T_2$. That such a minimum exist is already provided by the conditions (3) and (4) which brought the coating close to compensation (3) and allowed one to use polarization to perform fine adjustment of the F ratio and achieve high degree of temperature stability with condition (4). This scheme compensates for all temperature dependent phenomena in the light-source: From temperature dependence of the detector, the drift in the control circuitry, change in the beam shape of LED, and temperature dependence of the optical constants of the beam-splitter, lenses, and polarizer.

In the first embodiment of the present invention, an optical light source comprises an optically transparent beam splitter comprising a first surface, said first surface having a plane of incidence; an optical interference coating disposed on said first surface; a photodetector; a light-emitting diode operatively configured to emit a light beam, said light beam directed from said light-emitting diode to said first surface of the optically transparent beam splitter, the optical interference coating reflecting a portion of the light beam to the photodetector and transmitting an output beam; a control circuitry electrically coupled to said photodetector and said light-emitting diode operatively configured to power said light-emitting diode; a polarizer having a polarization direction; wherein said polarizer is placed in the path of said light beam between said light-emitting diode and said optically transparent beam splitter.

In the second embodiment of the present invention, an optical light source comprises an optically transparent beam splitter comprising a first surface, said first surface having a plane of incidence; an optical interference coating disposed on said first surface; a photodetector; a light-emitting diode operatively configured to emit a light beam, said light beam directed from said light-emitting diode to said first surface of the optically transparent beam splitter, the optical interference coating reflecting a portion of the light beam to the photodetector and transmitting an output beam; a control circuitry electrically coupled to said photodetector and said light-emitting diode operatively configured to power said light-emitting diode; a polarizer placed in the path of said light beam between said light-emitting diode and said optically transparent beam splitter and having a polarization direction. Said optical light-source has furthermore a defined temperature range of operation; a temperature drift coefficient defined as the change in the output beam intensity per unit temperature at a given light-source temperature within said temperature range; at least a first polarization direction of said polarizer for which said temperature drift coefficient is negative for all light-source temperatures within said temperature range; a second polarization direction of said polarizer for which said temperature drift coefficient is positive for all light-source temperatures within said temperature range; wherein said second polarization direction is substantially perpendicular to said first polarization direction.

The third embodiment of the present invention the optical light-source of first embodiment is further described as having an optimal temperature dependence coefficient defined as the difference between the intensity of said output beam at first temperature and the intensity of said output beam at a second temperature divided by the average of the intensity of said output beam at first temperature and the intensity of said output beam at a second temperature; a first temperature dependence coefficient defined as the difference between the intensity of said output beam at first temperature and the intensity of said output beam at a second temperature divided by the average of the intensity of said output beam at first temperature and the intensity of said output beam at a second temperature with said polarization direction is set parallel to said plane of incidence; a second temperature dependence coefficient defined as the difference between the intensity of said output beam at first temperature and the intensity of said output beam at a second temperature divided by the average of the intensity of said output beam at first temperature and the intensity of said output beam at a second temperature with said polarization direction is set perpendicular to said plane of incidence; wherein said optimal temperature dependence coefficient is smaller than one of said first temperature dependence coefficient and said second temperature dependence coefficient.

Figure 4:
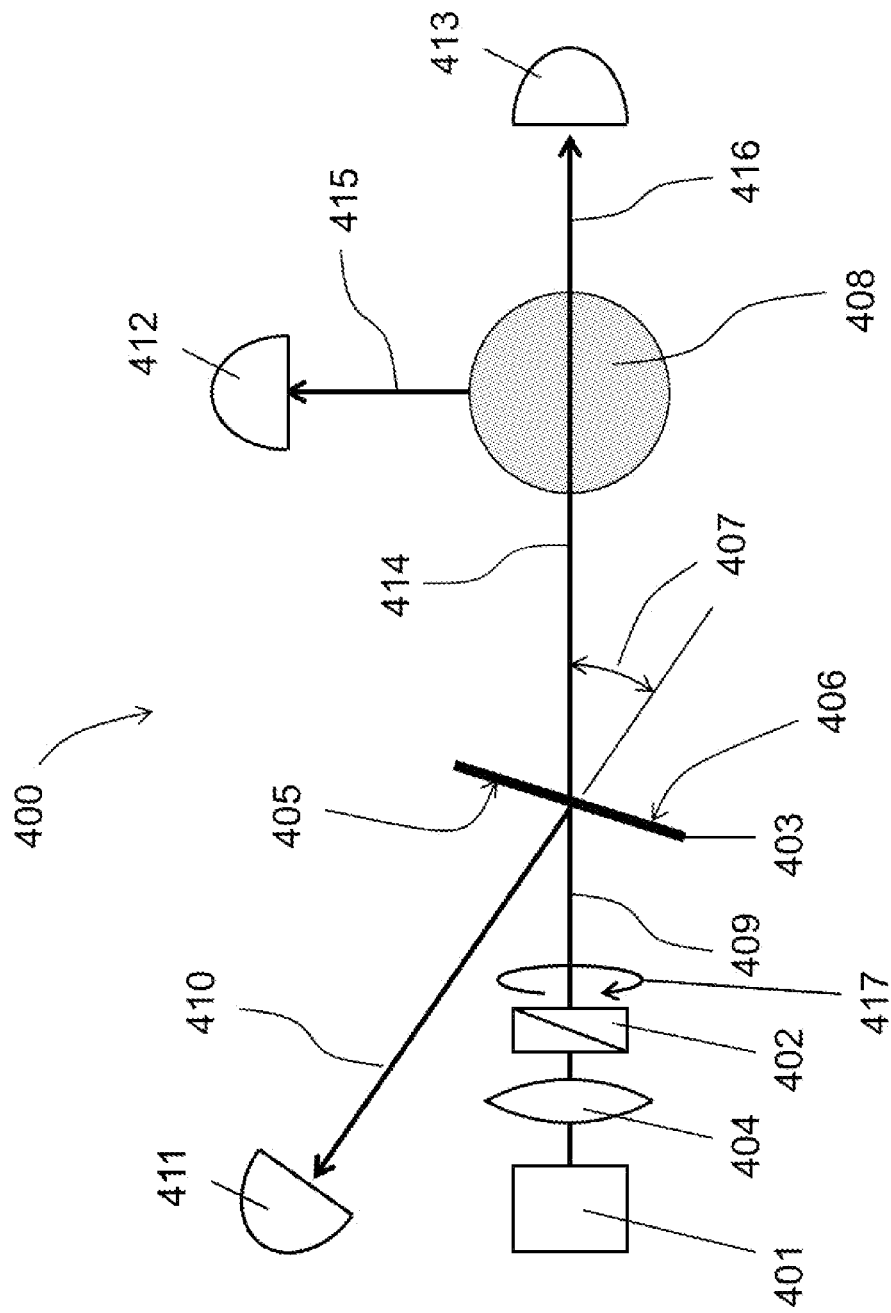
FIG. 4: An illustration showing an exemplary nephelometric turbidimeter using the present invention.

FIG. 4 illustrates a basic nephelometric turbidimeter architecture that takes advantage of the present invention. The exemplary turbidimeter 400 comprises of a light-emitting diode 401, a collimating lens 404, a polarizer 402 emitting a polarized incoherent beam 409 in the direction of a beam splitter 403. An interference coating 405 is disposed on the surface of the beam splitter 403 facing the light-emitting diode 401. The interference coating 405 reflects a portion 410 of the incident beam 409 towards a photo detector 411. The beam splitter may be a plate beam splitter or prism beam splitter. The back surface of the beam splitter 406 may be coated with an antireflective coating. The angle 407 between the incident beam 409 and the reflected beam 410 is typically 45 degrees, but may be lower because the sensitivity of the interference coatings to incidence angle reduces for smaller angles of incidence. With properly designed interference coating 405, the minimum temperature sensitivity of the output power beam 414 is adjusted by rotating the polarizer 402 to a suitable position and fixed. The polarizer rotation around its optical axis is illustrated with arrow 417. The transmitted beam 414 from the light source is incident on a vial or a transparent pipe with liquid 408. Due to turbidity, a portion of this light 414 is scattered 415 and detected by a nephelometric detector 412, while a portion of the light is detected by the transmission detector 413. FIG. 4 does not show the electronic circuitry needed to make this setup work. The light-emitting diode is powered by an electronic circuit that uses the current from the monitor photodetector 411 and a reference to maintain intensity of the beam 409 stable with temperature and aging. The output currents of the photodetectors 412 and 413 are used to determine the scattered and transmitted power using separate electronics. This arrangement may be used in a modulated four-beam method without departing from the spirit of invention.

Figure 5:
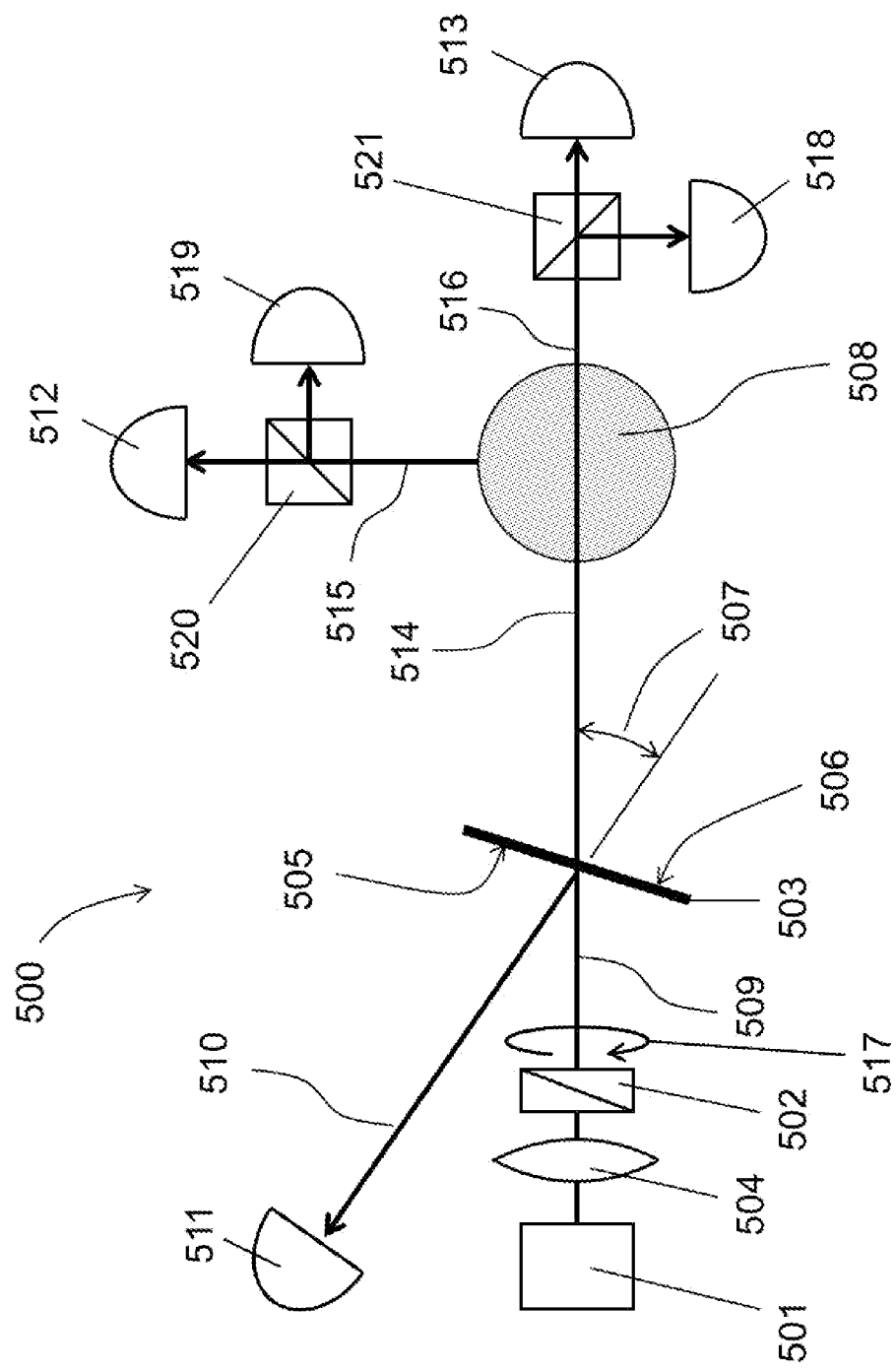
FIG. 5: An illustration showing an exemplary polarization-resolving nephelometric turbidimeter.

FIG. 5 illustrates a polarization resolved nephelometric turbidimeter architecture that takes advantage of the present invention. Scattering influences the polarization of light and it is sometimes important to characterize the polarization of the transmitted and scattered light. An exemplary turbidimeter 500 comprises of a light-emitting diode 501, a collimating lens 504, a polarizer 502 emitting a polarized incoherent beam 509 in the direction of a beam splitter 503. An interference coating 505 is disposed on the surface of the beam splitter 503 facing the light-emitting diode 501. The interference coating 505 reflects a portion 510 of the incident beam 509 towards a monitor photo detector 511. The beam splitter 503 may be a plate beam splitter or prism beam splitter. The back surface 506 of the beam splitter 503 may be coated with an antireflective coating. The angle 507 between the incident beam 509 and the reflected beam 510 is typically 45 degrees, but may be lower because the sensitivity of the interference coatings to incidence angle reduces for smaller angles of incidence. With properly designed interference coating 505, the minimum temperature sensitivity of the output power beam 514 is adjusted by rotating the polarization direction of the polarizer 502 to a suitable position and fixed. The polarizer direction rotation around its optical axis is illustrated with arrow 517. The transmitted beam 514 from the light source is incident on a vial or a transparent pipe with liquid 508. Due to turbidity, a portion of incident light 514 is scattered 515 and split into two orthogonally polarized beams on a polarization splitting beam splitter 520. Each of the two beams is detected by a separate detector 512 and 519. The beam splitter may also use an electro-optic effect to turn the polarization in which case a single detector may be used to detect both polarizations in a time-multiplexed arrangement. A portion of the incident light 514 is split into two beams of orthogonal polarization at a polarization splitting beam splitter 521. The two beams are detected by detectors 513 and 518. FIG. 5 does not show the electronic circuitry needed to make this setup work. The light-emitting diode is powered by an electronic circuit that uses the current from the monitor photodetector 511 and a reference to maintain intensity of the beam 409 stable with temperature and aging. The output currents of the photodetectors 512, 519, 513, and 518 are used to determine the scattered and transmitted power using separate electronics. This arrangement may be used in a modulated four-beam method without departing from the spirit of invention.

It is clear that this disclosed temperature-stable optical source can be used in many other applications besides turbidimetry and nephelometry without departing from the spirit of the invention. Thus, while particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

The invention claimed is:

1. A light source, comprising:
a light-emitting diode operatively configured to emit an unpolarized, incoherent light beam directed along an optical axis;
an adjustable polarizer positioned on said optical axis to intercept said light beam, said polarizer being operatively configured to polarize said light beam along a polarization direction perpendicular to said optical axis;
a beam splitter positioned on said optical axis to intercept said light beam after passage through said polarizer, said beam splitter comprising a first optical surface operatively configured to reflect a first portion of said polarized light beam and to transmit a second portion of said polarized light beam therethrough, wherein a place of incidence of said light beam at said beam splitter includes said optical axis and is perpendicular to said first optical surface; and
a photodetector positioned to capture said first portion of said polarized light beam after reflection by said beam splitter and operatively configured to generate photocurrent proportional to an intensity of said captured first portion of said polarized light beam, wherein said first optical surface comprises an optical interference coating, said coating being characterized by a ratio of reflectivity to transmission that depends on polarization and wavelength such that a change of said ratio with wavelength for light polarized parallel to said plane of incidence is opposite to a change of said ratio with wavelength for light polarized perpendicular to said plane of incidence.

2. The light source of claim 1, further comprising an electronic circuit operatively configured to drive electric current through said light emitting diode, the magnitude of said electric current determined by a difference between said photocurrent and a reference current.

3. The light source of claim 1 further comprising a collimating lens positioned between said light-emitting diode and said beam splitter.

4. A light source operated at a temperature in a temperature range, comprising:
a light-emitting diode emitting an unpolarized, incoherent light beam directed along an optical axis;
an adjustable polarizer positioned on said optical axis to intercept said light beam, said polarizer being operatively configured to polarize said light beam along a polarization direction perpendicular to said optical axis;
a beam splitter positioned on said optical axis to intercept said light beam after passage through said polarizer, said beam splitter having an optical surface reflecting a first portion of said polarized light beam and transmitting a second portion of said polarized light beam therethrough, said first portion of said polarized light beam having a first intensity;
a photodetector capturing said first portion of said polarized light beam after reflection by said beam splitter and generating a photocurrent proportional to said first intensity; and
an electronic circuit powering said light emitting diode in proportion to a difference between said photocurrent and a reference current;
wherein said second first intensity increases with said temperature when said polarization direction is parallel to a first polarization direction, and said first intensity decreases with said temperature when said polarization direction is perpendicular to said first polarization direction and wherein a plane of incidence of said light beam at said beam splitter includes said optical axis and is perpendicular to said first optical surface, and wherein said first optical surface is characterized by a ratio of reflectivity to transmission that depends on polarization and wavelength such that a change of said ratio with wavelength for light polarized parallel to the plane of incidence is opposite to a change of said ratio with wavelength for light polarized perpendicular to said plane of incidence.

5. The light source of claim 4 further comprising a collimating lens positioned between said light-emitting diode and said beam splitter.

6. A method for minimizing temperature sensitivity of a light output from a light-emitting diode, comprising the steps of:

providing an operating-temperature range;

providing an adjustable polarizer;

providing a light-emitting diode operatively configured to emit an unpolarized, incoherent light beam having a peak emission wavelength, said peak emission wavelength being dependent on temperature;

providing a photodetector having a responsivity in said operating-temperature range;

providing a beam splitter comprising an optical surface characterized by a ratio of reflectivity to transmission that depends on polarization and wavelength such that a change in said ratio with wavelength for light polarized parallel to the plane of incidence of that light at the beam splitter is opposite to a change in said ratio with wavelength for light polarized perpendicular to said plane of incidence;

assembling a light source so that said light-emitting diode emits said unpolarized, incoherent light beam along an axis, said light beam passes through said polarizer, emerging from said polarizer to be intercepted by said optical surface, wherein said optical surface reflects a first portion of said intercepted light beam and transmits a second portion of said intercepted light beam, said first portion having a first light intensity, and said first portion impinging on said photodetector;

measuring, using said photodetector, a temperature variation of said first light intensity while said polarizer is rotated around its optical axis for a range of angles;

noting a first adjustable polarizer angle for which said second light intensity increases with temperature and noting a second adjustable polarizer angle for which said light intensity decreases with temperature; and adjusting, using electronic circuitry, the angular position of said polarizer relative to said axis to an angle that is between said first adjustable polarizer angle and said second polarizer angle to minimize said temperature variation.

7. The method of claim 6 further comprising, prior to said assembling, providing a collimating lens; wherein said assembling positions said collimating lens between said light-emitting diode and said beam splitter.

* * * * *